US00PP08028P

United States Patent [19]

McRae

[11] Patent Number: Plant 8,028

[45] Date of Patent: Nov. 10, 1992

[54] ASIATIC LILY NAMED IVORY PIXIE

[75] Inventor: Edward A. McRae, Woodland, Wash.

[73] Assignee: Cebeco Lilies, Inc., Aurora, Oreg.

[21] Appl. No.: 504,287

[22] Filed: Mar. 19, 1990

[51] Int. Cl.[5] ..... A01H 5/00

[52] U.S. Cl. ..... Plt./87.4

[58] Field of Search ..... Plt./68, 87.4

*Primary Examiner*—James R. Feyrer

*Agent, Attorney, or Firm*—Raymond Cranfill

[57] ABSTRACT

A new variety of asiatic lily hybrid having medium sized flowers of the chalice type particularly distinguished by the generally overall chartreuse yellow coloration of its tepals which are lightly brushed with a primrose yellow along the midrib of the inner one-third of the tepal body and on its margins, the flowers being produced profusely in a cluster on a strong, upright stem at a height of about 40 cm. above the base of the plant. This plant flowers annually during mid-season, but a very consistant crop can be produced throughout the year by forcing.

1 Drawing Sheet

BACKGROUND OF THE NEW PLANT

This new plant originated as a seedling hybrid resulting from the cross of an unnamed clone with pollen from an unnamed clone which resulted from a cross of the variety Lemon Glow and the variety Red Carpet both being unnamed plants grown in my lily plant collection maintained at Sandy, Oreg. for breeding purposes. This seedling was selected by me for propagation because of its good growth habit for pot plant culture, the unusual coloration of its flowers which are well-sized, and its abundant foliage which make a very attractive plant; and asexual propagation of this plant through several successive generations was done under my direction at Sandy, Oreg. both by scaling and by tissue culture with very satisfactory results which demonstrated that the novel characteristics of this new lily plant will hold true from generation to generation and appear to be firmly fixed. Propagation of this plant for commercial purposes is now being done by Oregon Bulb Farms, Inc. at Aurora, Ore.

DESCRIPTION OF THE DRAWING

This new variety of lily plant is illustrated by the accompanying drawing which, in full color, shows a three-quarter face view of a fully open flower and a bud which is about to begin opening, the color rendition being as nearly true as can be reasonably attained by conventional photographic procedures.

DESCRIPTION OF THE NEW PLANT

The following is a detailed description of my new variety of lily as observed by Aurora, Oreg., with color designations according to the R.H.S. Color Chart published by The Royal Horticultural Society of London, England.

THE PLANT

Origin: Seedling.

Parentage:

*Seed parent.*—An unnamed clone identified by the number OH-6.

*Pollen parent.*—An unnamed clone of a hybrid resulting from the crossing of the varieties Lemon Glow and Red Carpet. Neither of the parents is patented.

Classification: Asiatic Hybrid of the chalice type.

Form: Single stem from each bulb.

Height: About 35 to 40 cm. depending upon age of the bulb.

Growth: Vigorous, upright and strong.

Foliage:

*Quantity.*—Abundant.

*Size of leaf.*—About 3.5 to 7.5 cm. long and about 8 mm. to 1 cm. in width.

*Shape of leaf.*—Linear with entire margins.

*Texture.*—Leathery.

*Aspect.*—Glossy.

*Color.*—Upper side — Green 137-A. Under side — Yellow Green 146-A.

Bulbs:

*Size.*—Up to about 2.5 cm. in circumference for commercial use.

*Color.*—White.

THE BUD

Shape: Long ovoid with an obtuse apex.

Size: About 6.5 cm. in length and about 2 cm. in diameter.

Rate of opening: The bud opens slowly at maturity in response to light.

Color of tepals:

*When sepals first divide.*—Green-Yellow 1-D.

*When tepals begin to unfurl.*—Yellow 5-C.

Peduncle:

*Length.*—About 11 cm.

*Character.*—Strong.

*Color.*—Green 146-B.

THE FLOWER

Blooming habit: Annually and profusely at mid-season.

Size of flower: Medium.

*Diameter.*—About 13 cm.

*Depth.*—About 6.5 cm.

Borne: As a cluster with raceme arrangement.

Shape:

*When bloom first opens.*—Cup shaped.

*When bloom matures.*—A flatened cup.

Tepalage:

*Number.*—Six.
*Arrangement.*—Hexagonally and imbricated.
*Form.*—Elliptical with entire margins and acute apex.
*Texture.*—Leathery.
*Aspect.*—Satiny.
*Color.*—Outer tepals — body, Chartreuse Yellow 2-D with Primrose Yellow 4-D at the base. Inside tepals — body, Chartreuse Yellow 2-D with Primrose Yellow 4-D at the base.
*Spotting.*—Each tepal is marked with tiny greyed purple spots, 184-A, beginning at the center of the nectary and extending about one-quarter to one-third of the length of the tepal.

Pedicel:
*Length.*—About 3.5 to 4.5 cm.
*Color.*—Yellow-Green 146-A.
*Character.*—Very strong and upright, ascending upwardly to about 55° from the horizontal.

Discoloration after full bloom: Very little color change with age.
Persistance: About three weeks.
Fragrance: None.
Disease resistance: Resistant to fusarium and botrytis and virus tolerant as observed at Aurora, Oreg.

THE REPRODUCTIVE ORGANS

Stamens:
*Number.*—6.

*Arrangement.*—Typical of genus lilium.
*Anthers.*—Size: 1.6 cm. Color: Yellow-Orange 20-A.
*Filaments.*—Length: About 5 cm. Color: Yellow 8-D.
*Pollen.*—Color: Yellow-Orange 23-A.

Pistils:
*Number.*—1.
*Styles.*—Length: About 4.75 cm. Color: Greyed Red 181-C.
*Stigma.*—Color: Greyed Red 180-A.

Character of ovaries: Typical of the genus lilium.

FRUIT

Fertility: The fruit is fertile.
Shape: Ovoid.
Color at maturity: Soft Brown.

The keeping quality of the bulbs of this plant is excellent with no scorch or bud abortion problems observed. A very consistent crop can be produced by forcing throughout the year.

I claim:

1. A new and distinct variety of asiatic hybrid lily plant, substantially as herein shown and described, characterized by its relatively large flowers of a generally chartreuse yellow coloration and its relatively low height as a pot plant.

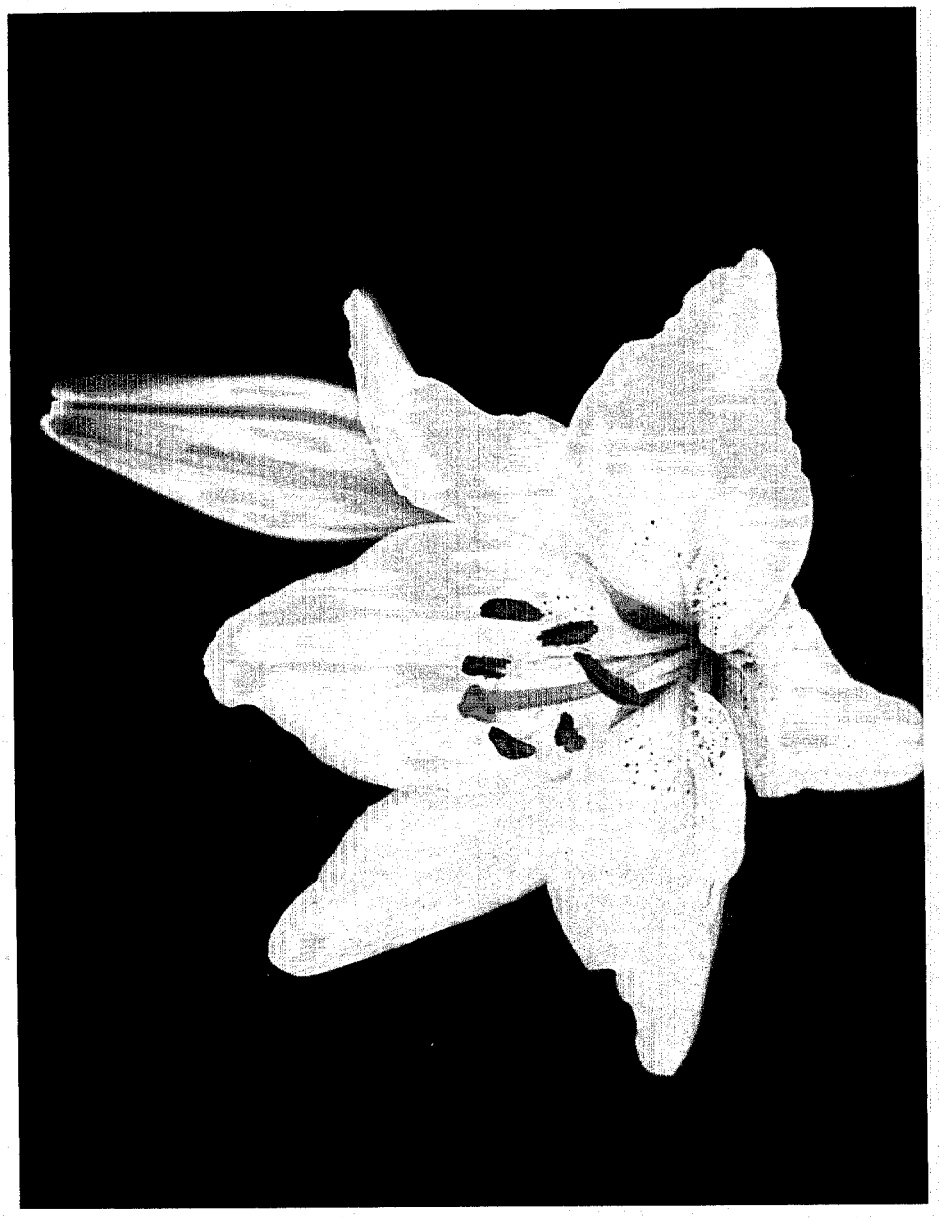

* * * * *